United States Patent [19]
Flock et al.

[11] Patent Number: 6,032,070
[45] Date of Patent: *Feb. 29, 2000

[54] METHOD AND APPARATUS FOR DETECTING ELECTRO-MAGNETIC REFLECTION FROM BIOLOGICAL TISSUE

[75] Inventors: Stephen T. Flock; Louis Fink; Milton Waner, all of Little Rock, Ark.

[73] Assignee: University of Arkansas, Little Rock, Ark.

[*] Notice: This patent is subject to a terminal disclaimer.

[21] Appl. No.: 08/483,480

[22] Filed: Jun. 7, 1995

[51] Int. Cl.[7] .............. A61B 5/00; A61B 5/103; A61B 1/00

[52] U.S. Cl. .............. 600/473; 600/476; 600/310

[58] Field of Search .............. 128/633, 637, 128/665, 666; 604/116, 20; 600/310, 317, 322, 473, 476, 479

[56] References Cited

U.S. PATENT DOCUMENTS

| | | | |
|---|---|---|---|
| 4,467,812 | 8/1984 | Stoller | 128/664 |
| 4,473,841 | 9/1984 | Murakoshi et al. | 358/98 |
| 4,556,057 | 12/1985 | Hiruma et al. | 128/665 |
| 4,570,638 | 2/1986 | Stoddart et al. | 128/665 |
| 4,621,283 | 11/1986 | Feinbloom | 358/93 |
| 4,817,622 | 4/1989 | Pennypacker | 128/664 |
| 4,945,239 | 7/1990 | Wist et al. | 250/358.1 |
| 4,948,974 | 8/1990 | Nelson et al. | 250/358.1 |
| 5,039,198 | 8/1991 | Vanbeek | 385/117 |
| 5,213,105 | 5/1993 | Gratton et al. | 128/665 |
| 5,279,297 | 1/1994 | Wilson et al. | 128/633 |
| 5,348,018 | 9/1994 | Alfano et al. | 128/633 |
| 5,361,769 | 11/1994 | Nilsson | 128/666 |
| 5,515,864 | 5/1996 | Zuckerman | 128/633 |
| 5,519,208 | 5/1996 | Esparza et al. | 250/226 |
| 5,598,842 | 2/1997 | Ishihara et al. | 600/322 |
| 5,625,458 | 4/1997 | Alfano et al. | 128/665 |
| 5,647,368 | 7/1997 | Zeng et al. | 128/665 |

FOREIGN PATENT DOCUMENTS

| | | | |
|---|---|---|---|
| 138398 | 4/1985 | European Pat. Off. | |
| 459712 | 12/1991 | European Pat. Off. | |
| 0266024 | 3/1989 | Germany | 128/666 |
| 2276732 | 10/1994 | United Kingdom | |
| 9211608 | 7/1992 | WIPO | |
| 9424927 | 10/1994 | WIPO | 128/633 |

*Primary Examiner*—William E. Kamm
*Assistant Examiner*—Carl H. Layno
*Attorney, Agent, or Firm*—Lyon & Lyon LLP

[57] ABSTRACT

A system and method is provided to view an anatomical structure such as a blood vessel in high contrast with its surrounding tissue. The system and method may be used to produce an image of an anatomical structure using reflected electromagnetic radiation singularly scattered from target tissue. The system and method may also provide same-side illumination and detection of reflected electromagnetic radiation in a convenient integral imaging device. The system and method may also provide helmet mounted imaging technology in a single integral helmet which allows the wearer to view an anatomical structure located within a patient such that the image is continuously oriented according to the orientation of the helmet wearer's head. The system and method may also be used in the performance of venipuncture. The system and method may provide for improved contrast between any anatomical structure and its surrounding tissue for use in any imaging system.

90 Claims, 3 Drawing Sheets

METHOD AND APPARATUS FOR DETECTING ELECTRO-MAGNETIC REFLECTION FROM BIOLOGICAL TISSUE

BACKGROUND OF THE INVENTION

The present invention relates to a system and method for locating anatomical structures within biological tissue. More particularly, the invention relates to a system and method for locating anatomical structures such as blood vessels in a mammalian body by utilizing equipment sensitive to the unique absorption and scattering characteristics of the target structure, such as blood. Further, the present invention provides a system and method to enhance the contrast between a target structure, such as a blood vessel, and its surrounding tissue.

Every day in the United States, many hundreds-of-thousands of medical procedures involving the puncturing of blood vessels are performed. Venipuncture, as it is known, is required in order to administer emergency fluids, blood components, and anesthetics during operations, or to allow the drawing of blood for biochemical analysis. Venipuncture, which is often the rate-limiting step when administering intravenous compounds, can take as long as a half hour with a typical patient or longer when the patient is a neonate, infant, geriatric, obese or burn patient. Notwithstanding the enormous financial burden on our society as a whole because operating rooms and health-care providers must wait as an intravenous line is placed, the delay in placing an intravenous line can in fact be life threatening. Furthermore, there is a high morbidity associated with multiple venipunctures caused by the clinician's failure to locate the vessel.

The reason venipuncture is sometimes difficult to do is that the blood vessels are often located relatively deep within the tissue which, because of its absorptive and scattering optical properties, makes visualization of the blood vessel impossible under normal conditions. Furthermore, the situation is made worse by the fact that the vessel may spasm and constrict if it is manipulated too much. Consequently, health care providers have a need to visualize blood vessels in real-time during venipuncture in order to reduce the risk to the patient, save time and reduce the cost of the procedure. Furthermore, reducing the time of the procedure limits the providers' exposure to a potentially contaminated needle. Finally, visualization of vascular tissue can provide important diagnostic and therapeutic information about certain diseases such as thromboses, cancers or vascular malformations.

In the mid-1970's an instrument was devised that purportedly provided surgeons with the ability of visualizing superficial blood vessels. It consisted of a visible light source which, when pressed up against the skin, transilluminated the subcutaneous tissue and aided in the visualization of superficial blood vessels. The blood-vessel transilluminator made use of the different absorption properties of blood and tissue. Because blood strongly absorbs certain wavelengths of light, while fat and skin absorb other wavelengths, a health-care provider purportedly could visually distinguish the position of the subcutaneous blood vessel with the naked eye. The transilluminator has essentially fallen into disuse because it fails to provide enough contrast between the blood vessel and tissue to be of use other than for venipuncture of superficial vessels. Furthermore, some versions of the blood-vessel transilluminator caused thermal damage to the patient.

The transilluminator's failure revealed that high contrast was of critical importance to medical personnel. Consequently, several references proposed using an illumination wavelength which penetrates surface tissue to a depth of the deep vessels but which is also highly absorbed by the blood. See, e.g., Cheong, W-F, et al., "A Review of the Optical Properties of Biological Tissues," *IEEE Journ. Quant. Elec.*, 26:2166–2185 (1990). These references, however, did not disclose efficient means of eliminating detection of scattered light from areas outside the vessel region (i.e., off angle light). Nor did they disclose the elimination of detection of polychromatic white noise, such as from ambient room light or from a polychromatic light source. Later devices only employed a subtraction technique using expensive digital processing and cumbersome computer analysis to eliminate unwanted scattered waves. Furthermore, these devices did not disclose a method of noise reduction for use with a white light source, but rather relied on use of a monochromatic laser light source to reduce polychromatic noise. Accordingly, there was a need for a contrast enhancement device usable with a polychromatic light source or in a polychromatic clinical environment.

Most importantly, electromagnetic imaging devices have used transmitted rather than reflected light to construct their image. Such systems house the image detector and the light source on either side of the patient rather than side by side in a single integral unit. Such an arrangement unfortunately does not allow for convenient same-side illuminating and detecting such as in the form of a single unit goggle or scanning device. Accordingly, manipulation of many of these devices along with the patient required multiple clinical personnel. Moreover, these references in fact teach away from the use of any scattered light to create an image, including reflected light. Instead, these devices seek to eliminate all scattered light from detection since such light was thought not to carry any image information.

SUMMARY OF THE INVENTION

In the present invention, a system and method is provided to view an anatomical structure such as a blood vessel in high contrast with its surrounding tissue. It is an object of the invention to produce an image of an anatomical structure using reflected electromagnetic radiation singularly scattered from the target tissue.

Yet another object of the present invention is to provide a method and apparatus for producing a clear three-dimensional image of an anatomical structure by detecting the electromagnetic radiation characteristics reflected from the target area.

Another object of the invention is to provide same-side illuminating and detecting of reflected electromagnetic radiation for use in a convenient integral imaging device.

Still another object of the present invention is to provide helmet mounted imaging technology in a single integral helmet which allows the wearer to view an anatomical structure located within a patient such that the image is continuously oriented according to the orientation of the helmet wearer's head.

Yet another object of the present invention is to provide a method and apparatus for quickly, accurately and efficiently allowing for the performance of venipuncture.

Another object of the present invention is to provide a method and apparatus for improving contrast between any anatomical structure and its surrounding tissue for use in any imaging system.

These and other objects of the present invention are achieved by one or more of the following embodiments.

DESCRIPTION OF THE INVENTION

Figure 1:
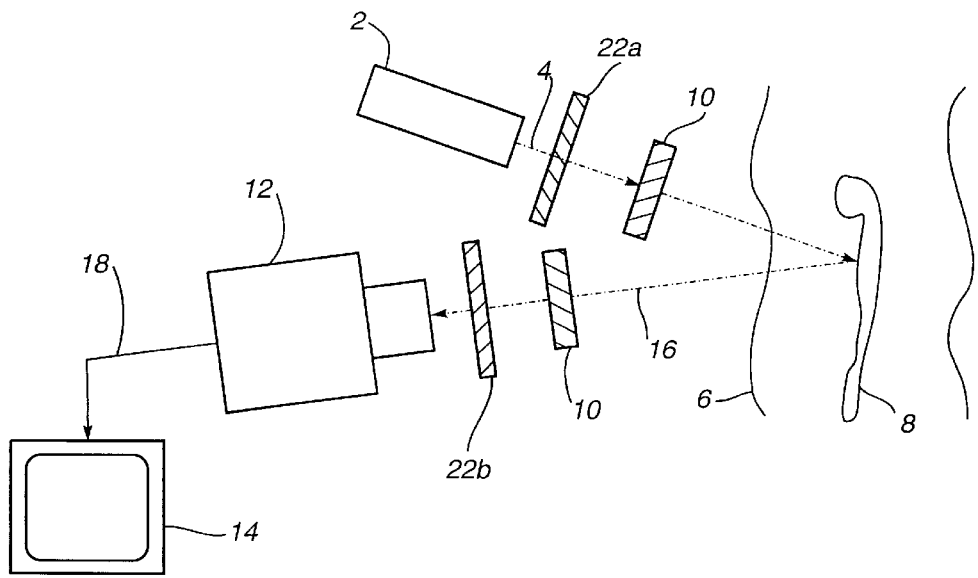
FIG. 1 is a schematic diagram of the basic imaging system constructed in accordance with the principles of the present invention.

The present invention provides a system for locating an anatomical structure, such as a blood vessel, wherein the system comprises a light source and an image detector, which detects light radiation reflected from the area of examination, and a monitor which receives and displays image information from said image detector. The term "light source" includes but is not limited to polychromatic sources, such as white light sources, as well as monochromatic sources such as laser light sources. The term "image detector" refers to any device capable of detecting light, including but not limited to charge-coupled device infrared cameras (CCD's), video cameras, and liquid crystal television detectors.

Optionally, the present invention may include elements that enhance the contrast between the anatomical structure and the surrounding tissue in the image. The term "contrast enhancing element" refers to any element or combination of elements which enhance contrast between the anatomical structure and its surrounding tissue in the image, including elements which eliminate light outside the wavelengths of interest and elements which reduce multiply scattered light from the biological tissue in the tissue region of interest or eliminate multiply scattered light from the biological tissue adjacent to the region of interest. The contrast enhancing element as herein defined includes, but is not limited to, bandpass filters, digital processing filters, collimators, polarizing optical elements, photorefractive crystals, digital frame grabbers, blink imaging monitors, phase modulators, confocal-optical devices, exogenous dyes, and vascular modifying procedures.

The instant invention of detecting reflected light allows the light source and the reflected image detector to be part of a single integral unit. Such a single unit provides for convenient use, allowing a caregiver to hold the unit or wear the unit and as in the form of a helmet. As explained in greater detail below, the possibility of a single integral unit also provides for the creation of a helmet capable of producing a real-time three-dimensional image of an area inside a patient in a manner that directly corresponds to the helmet wearer's line of vision.

In one variation of this aspect of the invention, a single integral unit comprises a helmet, at least one light source and at least one imaging detector mounted on the helmet. Additionally, the helmet may contain a monitor, such as a monitor within an eye piece, which displays the contrasted image of the anatomical structure being viewed by the helmet wearer. In a preferred embodiment, two imaging detectors mounted onto eyepieces of the helmet receive electromagnetic radiation information reflected from the patient. The light source may optionally be coupled to an optical filter bundle, the end of which is pressed against the skin so as to reduce specular reflection. The information is then used to create a three-dimensional image for real-time transmission to a monitor such as a monitor contained within an eyepiece of the headgear. Such embodiment allows the wearer to see the contrasted structure within a patient in a way which corresponds to the wearer's own line of vision.

In another embodiment of the invention, the image detector and light radiation source are part of a single integral scanning device which is passed over the area of interest. In this embodiment the single scanning device can be a hand-held scanner or a movable mounted scanner, either one attached to a portable monitor. Such an embodiment allows for mobile scanning by a caregiver. In another embodiment the monitor itself can be part of the scanner.

According to a second feature of this invention, a variety of embodiments can be used to enhance contrast between the anatomical structure and its surrounding tissue. In one such embodiment the light source projects a broad range of wavelengths, including wavelengths absorbed by the anatomical structure, such as between approximately 700–900 nm for blood. The light is then passed through a bandpass filter which passes only the desired wavelengths, e.g. 700–900 nm. The light is subsequently absorbed by the target structure, e.g. the blood vessel tissue, but not its surrounding tissue. Alternatively, the filter may be placed in the path of the reflected light before it reaches the detector, thus eliminating polychromatic noise. The imaging detector then sends a signal to an image monitor. In a preferred embodiment the imaging detector is a CCD camera.

In another contrast enhancing embodiment, a laser which produces radiation at a single wavelength within the desired range, e.g. 700–900 nm, is used as the source of illumination. The target tissue including the target anatomical structure, such as the blood vessel, is irradiated with light. Only unabsorbed light within the important range is then reflected back to the image detector. Such embodiment allows for reduction of any other polychromatic light which serves as a source of background noise in the image. Specific wavelengths such as 730 nm for bilirubin, 1158 nm and 1210 nm for fat, and 760 nm for hematomas may be used to detect other anatomical structures.

In another embodiment, a polarizing optical element such as a polarizing prism can be added to or can replace the bandpass filter. By polarizing the light before it reaches the tissue the reflected light will also be polarized in a particular plane with respect to the tissue. Thus, a polarizing optical element placed in front of the detector can preferentially select out such radiation reflected by the tissue with the same polarization. Any highly scattered light (noise) and specular reflection will be filtered out since highly scattered light is randomly polarized and specular reflection is predominantly polarized in a different plane than the incident light. This polarizing element embodiment may be used with transilluminated light detection systems as well as reflected light detection systems.

In another embodiment, collimators are used to eliminate much of the reflected radiation that is highly scattered. In a variation of this embodiment, both the source and detector are scanned in a raster-type pattern with the image built up over the period of the raster scan. This variation allows for strong collimation of the reflected light.

In another embodiment, a confocal imaging system is focused at a particular depth of interest. Light from different depths and different positions is rejected by use of a collimator at the focal point of the optics. The image is then built up by raster-scanning the object to be imaged.

In still another embodiment, the tissue is illuminated at two wavelengths, one which is strongly absorbed by the target structure but not the surrounding tissue and one, with approximately the same scattering efficiency, that is weakly absorbed by both the target structure and the surrounding tissue. The two images are sequentially captured with a digitizing frame grabber, stored and subtracted from one another. The resultant image lacks the effects of scatter present in each image since scattered light is subtracted out. In a variation, two wavelengths alternate illuminating the target and being displayed on the monitor. The viewer sees images fed to the monitor in alternating fashion. Because the human eye is especially sensitive to relatively rapid changes in light intensity, the viewer is sensitive to the highly contrasted anatomical structure image. This blink imaging process eliminates the need for expensive digital electronic processing to subtract the signals.

In another embodiment, the source illumination is phase modulated by connecting a modulation source to a light phase modulator such as a Kerr cell. The modulation source also modulates the image detector such that the detector measures only electromagnetic radiation that has the same state of modulation as the incident light. This embodiment has the advantage that highly scattered light, devoid of image information, is phase-shifted. Consequently, highly scattered light will not be detected. In another embodiment the modulation is accomplished by varying illumination intensity rather than the illumination phase such as by modulating the diode laser power supply. (e.g. with the Model S1011 diode laser modulating power supply from Thor-Labs, Newton, N.J.). Both of these modulation embodiments may be used with transilluminated light detection systems as well as reflected light detection systems.

In still another embodiment to enhance image contrast, an exogenous dye is administered to the patient which then collects within the anatomical structure of interest. The exogenous dye is highly absorptive of a particular wavelength of light relative to the surrounding tissue. An image prior to dye application can be taken and then subtracted from an image taken after dye application. Such a method subtracts out the unwanted noise common to both images and leaves only an enhanced image. Alternatively, the images can be alternately displayed so that the operator views the highly contrasted image by virtue of the aforementioned blink imaging process. In another embodiment the exogenous dye is collected by the surrounding tissue but not the anatomical structure of interest thereby creating image contrast.

In another embodiment the image detector is a liquid-crystal television detector such as available from Sony Electronics, Inc. Itasca, Ill. The liquid crystal television detector can provide phase sensitive detection. See e.g., Alliance for Photonic Technology Industrial Quarterly, Vol.3, no.2, p.3 (Winter/Spring 1995). In this embodiment the light source is phase modulated in synchronicity with the detector such that the detector captures only the light modulated at the same frequency and ignores all other light. Consequently, highly scattered light which has phase shifted with respect to the incident source light, is eliminated.

In yet another embodiment the image detector is a liquid crystal television detector which captures all phase information. However, instead of phase modulating the incident light, the detector captures light of all phases, and then sends phase information along with intensity information to a device which is used to construct a three-dimensional image of the anatomical structure. By capturing phase information this embodiment can do real-time holography in three dimensions. In a variation of this three-dimensional image embodiment a photorefractive crystal or polymer (e.g. Lithium Niobate from CSK Optronics, Culver City, Calif.) is directly used as an image detector to capture the image. A hologram image is then created by illuminating the crystal or polymer in real-time. Alternatively, the crystal or polymer may receive its input from the output of the liquid crystal television detector.

DETAILED DESCRIPTIONS OF THE PREFERRED EMBODIMENTS

An imaging system constructed in accordance with the principles of the present invention is shown in FIG. 1, and includes a light source 2 radiating a beam of incident light 4 upon a biological tissue 6, such that the beam is partially transmitted through the biological tissue until being absorbed by the target anatomical structure 8. An image detector 12, (e.g. Model CCD-72 camera available from Dage-MTI, Inc.) detects reflected light 16, predominantly reflected from tissue surrounding the target anatomical structure with a different absorptive wavelength than the anatomical structure. The image detector 16 is connected by a video signal 18 to a monitor 14 so that the intensity information of incident light reflected from the tissue is displayed onto the monitor in the form of an image. If a polychromatic light source is used, wavelengths outside the useful range for imaging the target structure should be filtered out by one or more bandpass filters 10. Alternatively, the imaging detector can detect only wavelengths within the useful range, such as occurs with a charge-coupled device infrared camera (CCD) (e.g. CCD1350-1 infrared CCD camera and 9300-00 image intensifier available from Electrophysics Corp. Fairfield N.J.). Alternatively, a real-time digital image processor, such as described in FIG. 2, (e.g. CSP-2000 Processor available from Dage-MTI Inc.) can be used to filter out information poor wavelengths generated by the polychromatic light source.

In an alternative embodiment of the invention, a polarizing optical element 22a such as a polarizing filter (e.g. available from Ealing Electro-Optics Ind., Holliston, Mass. or Oriel Corp., Stratford, Conn.) is used in combination with a laser or other monochromatic light source. Monochromatic sources include, by way of example, the Model 6124 laser diode available from New Focus, Inc. Sunnyvale Calif., the Model Micralase available from Micracor, Inc., Acton Mass., and the MDL-DLAW10 available from McDonnell Douglas Aerospace, St. Louis Mo. The polarizing filter, by polarizing the incident light in a particular plane with respect to the tissue will cause the singularly reflected light to be of a distinct polarization. A second polarizing optical element 22b in front of the detector then preferentially selects out singularly reflected radiation from the light source. Multiply scattered radiation, which carries little image information, is typically randomly polarized and thus will not pass through the second polarizing optical element 22b and onto the image detector 12. The polarizing filters can be used with either the bandpass filter 10, the charge-coupled device infrared camera, the digital image processor of FIG. 2 or any combination of these three in the event a polychromatic light source is used for the light source 2. Any combination of these elements may also be used when the light source 2 comprises a laser or other monochromatic light source.

Figure 2:
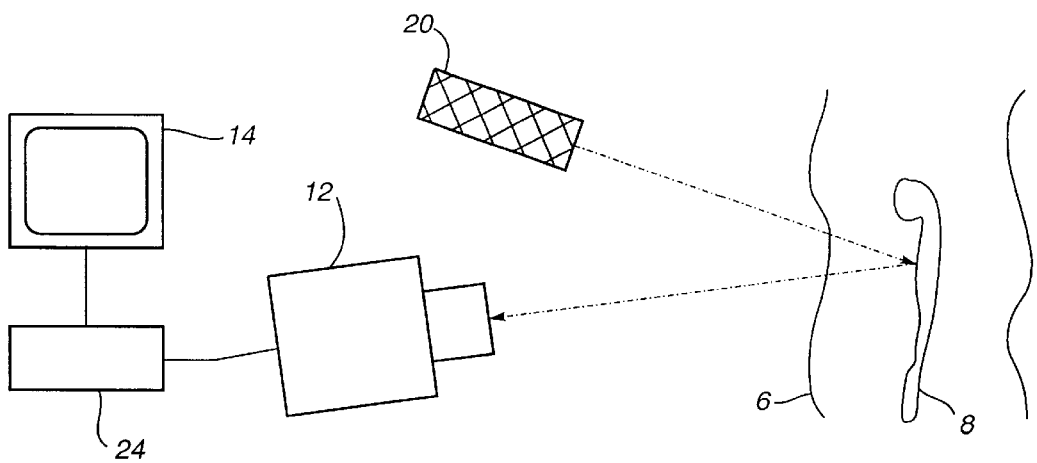
FIG. 2 is a schematic diagram of a further embodiment disclosing a light source emitting two distinct wavelength ranges and a digital image processor and frame grabber for enhancing image contrast.

A further embodiment of the invention is shown in FIG. 2 for an imaging system with a digital image processor and frame grabber 24 (such as the CSP-2000 processor available from Dage-MTI Inc.). In this embodiment the tissue can be illuminated by a light source 20 projecting at least two wavelengths. In a preferred embodiment the biological tissue 6 is illuminated by a wavelength that penetrates the tissue yet is weakly absorbed by the target anatomical structure 8. In the case of a blood vessel containing blood, the wavelength of between 700 nm and 900 nm, preferably around 800 nm, would suffice. The reflected image is then captured with a digital image processor, containing a digital frame grabber, and stored. Next, the same tissue field is illuminated by a second wavelength which is close enough in frequency to the first wavelength such that the tissue scattering efficiency is about the same. However the second wavelength must either be more weakly or more strongly absorbed by the target anatomical structure. This second image is captured and subtracted from the previous by the digital image processor 24; thus the effects of scatter are removed from the resulting image and only the absorption difference between the two images shows.

Another embodiment of the two-wavelength approach eliminates the digital image processor 24 altogether. By illuminating the biological tissue with two wavelengths and alternating the display of the image reflected by each separate wavelength on the monitor 14 the target anatomical structure will sequentially appear and disappear. The human eye is especially sensitive to relatively rapid changes in light intensity, and through a physiological process known as blink imaging would detect the outline of the target structure.

Figure 3:
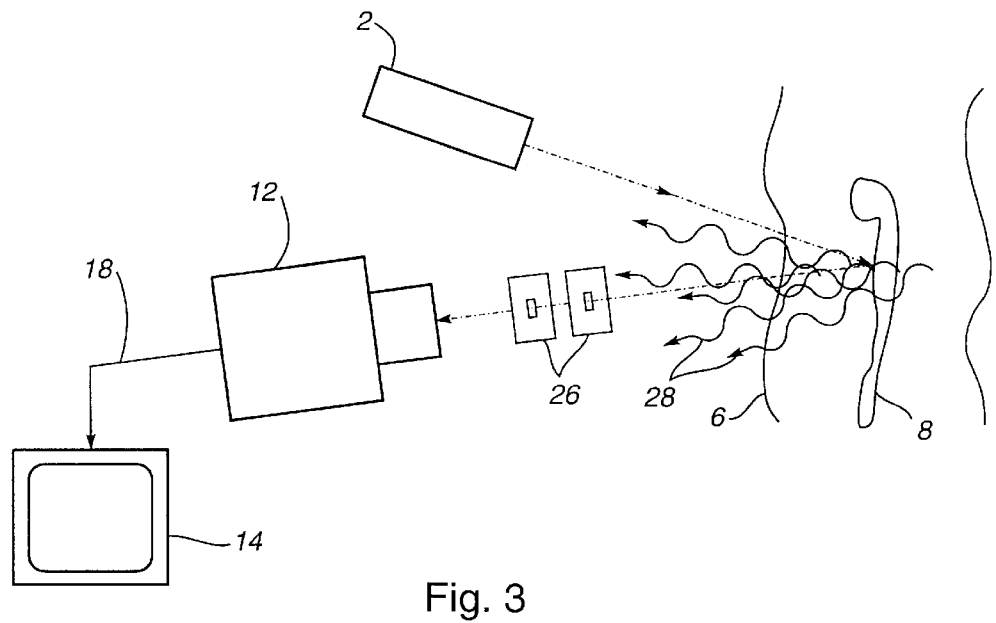
FIG. 3 is a schematic diagram of a further embodiment disclosing a system using collimators to eliminate multiply scattered light.

A further embodiment of the invention is shown in FIG. 3, disclosing a system using collimators to eliminate multiply scattered light. Components corresponding to those already identified in connection with FIG. 1 have the same reference numerals. In this embodiment at least one collimator 26 is used to stop multiply scattered photons 28 from reaching the image detector 12. In this way, strong collimation reduces the background noise not useful for producing an image. Extremely strong collimation, if required, might necessitate the light source and image detector to be scanned in a raster-type pattern and the image built up over the period of a raster scan. The collimators may be used in combination with any of the possible combinations of contrast enhancing elements shown in FIG. 1 and FIG. 2. When the light source 2 is polychromatic, the collimators should be used in combination with a bandpass filter 10, a selective image detector 12 such as a infrared CCD, a digital image processor 24, or any other device capable of eliminating reflected light outside the wavelength of interest.

Figure 4:
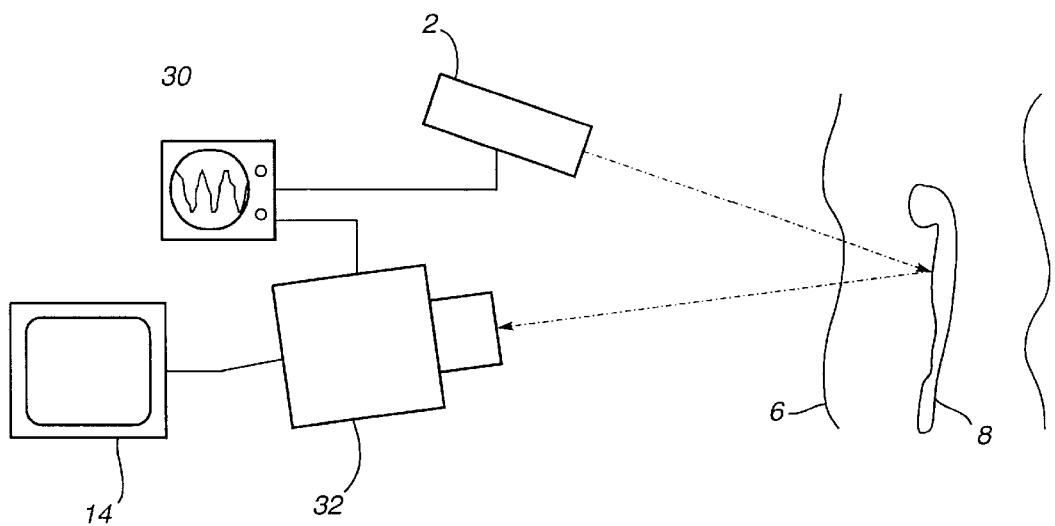
FIG. 4 is a schematic diagram disclosing a system for performing phase-modulated detection of a reflected image.

Another embodiment of the invention is shown in FIG. 4 disclosing a system for performing phase-modulated detection of a reflected image. In this embodiment, incident laser light is phase modulated by a modulation source 30 which controls a light phase modulator 28 such as a rotating aspheric optic or a Kerr cell (e.g. available from Meadowlark Optics, Longmont Colo., Advanced Optronics Inc., San Jose Calif., or Ninds Instruments Inc., Nillsboro Oreg.) The modulation source 30 controls the phase-sensitive imaging detector 32 such as a liquid crystal video television. Thus, the image detector only measures the reflected light that has the same state of modulation as the incident light. All other light is removed from the measurement. Because highly scattered light is phase-shifted, that light too would also be eliminated. The modulation source 30 may also comprise two independent phase-matched sources, one controlling the modulator 28 and one controlling the detector 32.

Figure 5:
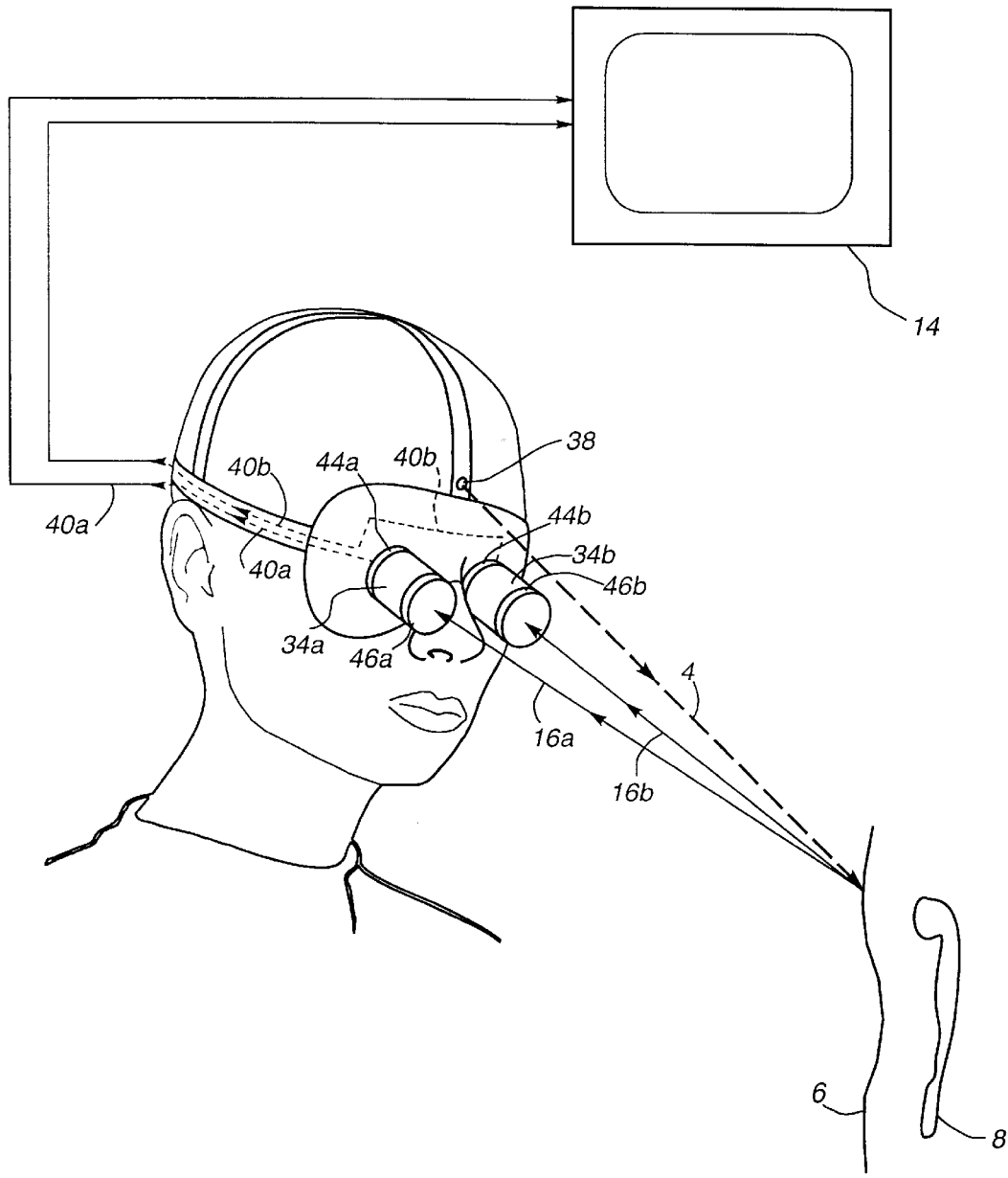
FIG. 5 is a schematic diagram of an imaging helmet apparatus in accordance with the principles of the present invention.

A further embodiment of the invention is shown in FIG. 5 which discloses a system of conducting binocular stereo imaging of a target anatomical structure. In this preferred embodiment, three dimensional depth information is incorporated within the image by detecting two angles of reflected light from the target tissue area using two imaging detectors 34a and 34b (e.g. Model 8900 infrared sensitive video cameras with focussing eyepieces and objective lenses from FJW Optical Systems Inc., Palatine, Ill.) In one variation of this embodiment a light source 38 (e.g. MDL-DLAW10 diode laser from McDonnell Douglas Aerospace, St. Louis, Mo., with LD1001 driver from Thor-Labs, Newton N.J. and 12 V DC source) is mounted on a helmet 40 (e.g. The Physician's Headlight from Welch-Allyn Inc., Skaeneateles Falls, N.Y.) which in turn holds the two imaging detectors 34a and 34b. The light source output may optionally be focussed with diode laser collimation optics (e.g. Model LT110P-B from Thor-Labs, Newton, N.J.) to produce about a 1 mm spot at a distance of about 20 inches. The incident light 4 is reflected back from the target tissue as 16a and 16b.

In a variation of the preferred embodiment bandpass filters 46a and 46b (e.g. 808 nm center wavelength filters Model BP Series-3 Cavity from Omega Optical, Inc., Brattleboro, Vt.) are positioned in front of the video cameras to filter out all ambient light. In another variation, linear polarizing filters (e.g. Model 27805 filters, from Oriel Corp., Stratford, Conn.) are placed, one between the laser light source and the tissue and the others on each eyepiece, thereby eliminating scattered (randomly polarized) light. The detectors each capture light reflected back at a slightly different angle creating a stereoscopic effect. The image detector's output 40a and 40b send the information to a monitor 14 for processing and eventual three-dimensional display of the highly contrasted tissue area. In a variation of this embodiment, the monitors may actually be in the eyepieces, 44a and 44b of the helmet, such as attached to or part of the image detectors 34a and 34b, thus allowing the goggle wearer to examine the subject as if seeing through the tissue surrounding the target anatomical structure.

In another variation of this embodiment, the two image detectors are mounted on an automated piece of surgical equipment. The output of the detectors 34a and 34b are sent to a remote monitor which displays a three-dimensional image of the target tissue. The surgical equipment is then operated remotely using position-sensitive servo-motors. Accordingly, certain procedures such as venipuncture can be done remotely by the operator.

In another embodiment, image contrast is enhanced by the injection of an exogenous dye which is collected in the anatomical structure of interest. Alternatively, the exogenous dye is collected in the surrounding tissue but not the anatomical structure of interest. For example, indocyanine-green (ICG) dye absorbs strongly near 800 nm, where tissue is relatively transmitting. Flock, S. et al., "Thermal Damage of Blood Vessels using Insocyanine Green and a Pulsed Alexandrite Laser," *Lasers Med. Sci.,* 8:185–196 (1993). A reflected image is taken using an 800 nm illumination source. Then ICG is injected upstream, and a second image is taken. The first image is stored by the digital processor and the second image subtracted out by a digital processor and the result displayed as previously described. Alternatively, the operator can monitor the image using the blink imaging process as previously described without the aid of digital processing. Other exogenous dyes such as hematoporphyrin can also be used.

In a variation of this embodiment, a monoclonal antibody to a particular antigen is linked to a light absorbing chromophore. The antibody is then bound to the target tissue of interest. The target area is then illuminated with light of a wavelength absorbed by the chromophore and the resultant image detected. Alternatively, a wavelength which excites a fluorophore bound to antibody may be used whereupon fluorescence of the fluorophore is detected. This technique can create an image of any subcutaneous pathology bindable through antibody technology. For example, a monoclonal antibody to a hepatocyte cell surface antigen is injected and an image of the liver can be created by the present invention. Such a technique may be used in conjunction with any of the aforementioned systems and combinations.

In another variation of this embodiment, molecules with plaque or cholesterol affinity may be injected into the blood stream. These molecules then collect on plaque in the blood vessels. Hayashi et al., "Transadvential Localization of Atheromatous Plaques by Fluorescence Emission Spectrum Analysis of Mono-L-aspartyl-chlorin e6," *Cardiovasc. Research,* 27:1943–1947 (1993). In this variation, an illumination wavelength is selected based upon the differential absorbance of the drug or, alternatively, the drug's capacity for florescence at a particular wavelength. The contrast image is then detected by the image detector after illumination at the appropriate wavelength.

In still another variation of this embodiment, images are taken of a blood vessel before a vascular modifying procedure is performed. For example, a tourniquet can be applied to the vessel after a first image detection, thus modifying blood density. A second image then is detected and subtracted from the first image. Alternatively, ice can be applied to the cutaneous surface after a first detection, thus modifying blood flow. Again, the post-modifying procedure image is subtracted from the pre-modifying procedure image to create the outline of the vessel.

Although modifications and changes may be suggested by those skilled in the art, it is the intention of the inventors to embody within the patent warranted hereon all changes and modifications as reasonable and properly come within the scope of their contribution to the art.

We claim as our invention:

1. An imaging apparatus comprising a light source wherein said light source comprises a monochromatic source within the infrared range and wherein said monochromatic light source within the infrared range comprises means for illumination within the range of 700–900 nm;
   an image detector which detects light from said light source after it has been reflected from a biological target tissue; and
   a monitor which displays an image of an internal anatomical structure from said image detector.

2. An imaging apparatus comprising a light source;
   an image detector further comprising a video camera which detects light from said light source after it has been reflected from a biological target tissue; and
   a monitor which displays an image of an internal anatomical structure received from said image detector.

3. An imaging apparatus comprising a light source;
   an image detector further comprising a liquid crystal television detector which detects light from said light source after it has been reflected from a biological target tissue; and
   a monitor which displays an image of an internal anatomical structure received from said image detector.

4. An image apparatus comprising a light source;
   an image detector which detects light from said light source after it has been reflected from a biological target tissue;
   a contrast enhancing element wherein said contrast enhancing element includes at least one bandpass filter and a monitor which displays an image of an internal anatomical structure received from said image detector.

5. An imaging apparatus comprising a light source;
   an image detector which detects light from said light source after it has been reflected from a biological target tissue;
   a contrast enhancing element wherein said contrast enhancing element includes at least one bandpass filter which passes wavelengths around 800 nm; and
   a monitor which displays an image of an internal anatomical structure received from said image detector.

6. An imaging apparatus comprising a light source:
   an image detector which detects light from said light source after it has been reflected from a biological target tissue:
   a contrast enhancing element wherein said contrast enhancing element includes a digital processor filter; and
   a monitor which displays an image of an internal anatomical structure received from said image detector.

7. An imaging apparatus comprising a light source;
   an image detector which detects light from said light source after it has been reflected from a biological target issue:
   a contrast enhancing element wherein said contrast enhancing element includes at least one collimator; and
   a monitor which displays an image of an internal anatomical structure received from said image detector.

8. An imaging apparatus comprising:
   a light source;
   an image detector which detects light from said light source transmitted through biological target tissue;
   a monitor which receives and displays image information from said image detector; and
   a contrast enhancing element which includes a first polarizing optical element in the path of incident light between said light source and said biological tissue and a second polarizing optical element in the path of the transmitted light between the non-light source side of the tissue and said image detector.

9. An imaging apparatus comprising:
   a light source;
   an image detector which detects light from said light source reflected from a biological target tissue;
   a monitor which receives and displays image information from said image detector; and
   a contrast enhancing element which includes polarizing optical element in the path of incident light between said light source and said biological tissue and a polarity selecting optical element in the path of the reflected light between the said biological tissue and said image detector.

10. An imaging apparatus comprising:
    a light source;
    an image detector which detects light from said light source transmitted through biological target tissue;
    a monitor which receives and displays image information from said image detector; and
    a contrast enhancing element including a modulation source and a light phase modulator connected to said modulation source.

11. An imaging apparatus comprising:
    a light source;
    an image detector which detects light from said light source reflected from a biological target tissue;

a monitor which receives and displays image information from said image detector; and a contrast enhancing element including a modulation source and a light phase modulator connected to said modulation source.

12. An imaging apparatus comprising:

a light source;

an image detector which detects light from said light source reflected from a biological target tissue;

a monitor which receives and displays image information from said image detector; and a contrast enhancing element including an illumination intensity modulation source.

13. An imaging apparatus comprising a light source;

an image detector which detects light from said light source after it has been reflected from a biological target tissue wherein said light source and said image detector are part of a single integral unit; and a monitor which displays an image of an internal anatomical structure received from said image detector.

14. An imaging apparatus as in claim 13 wherein said single integral unit comprises a helmet.

15. An imaging apparatus as in claim 14 wherein said monitor comprises part of said helmet.

16. An imaging apparatus as in claim 14 wherein said light source is coupled to said optical fiber bundle.

17. An imaging apparatus as in claim 14 wherein said image detector comprises an infrared sensitive video camera and said light source comprises a diode laser.

18. An imaging apparatus as in claim 14 wherein said single integral unit comprises an automated piece of surgical equipment.

19. An imaging apparatus comprising:

a light source wherein said light source comprises a dual-wavelength illumination source and said imaging apparatus further comprises an optical fiber bundle wherein said light source is coupled to said optical fiber bundle;

an image detector which detects light from said light source after it has been reflected from a biological target tissue;

a contrast enhancing element; and a monitor which displays an image of an internal anatomical structure received from said image detector.

20. An imaging apparatus comprising:

a light source wherein said light source comprises a dual-wavelength illumination source;

an image detector which detects light from said light source after it has been reflected from a biological target tissue;

a contrast enhancing element; and a monitor which displays an image of an internal anatomical structure received from said image detector wherein said monitor comprises a means to rapidly alternate the display of the image reflected at each respective wavelength.

21. An imaging apparatus comprising a light source;

an image detector which detects light from said light source after it has been reflected from a biological target tissue;

a contrast enhancing element wherein said contrast enhancing element includes an exogenous dye adsorbed within the biological target tissue; and a digitizing frame grabber connected to said image detector.

22. An imaging apparatus comprising a light source;

an image detector which detects light from said light source after it has been reflected from a biological target tissue;

a contrast enhancing element wherein said contrast enhancing element includes a monoclonal antibody attached to the target biological tissue;

a digitizing frame grabber connected to said image detector; and a monitor which displays an image of an internal anatomical structure received from said image detector.

23. An imaging apparatus comprising a light source;

an image detector which detects light from said light source after it has been reflected from a biological target tissue;

a contrast enhancing element wherein said contrast enhancing element includes a molecule collected on plaque within a blood vessel;

a digitizing frame grabber connected to said image detector; and a monitor which displays an image of an internal anatomical structure received from said image detector.

24. An imaging apparatus comprising a light source;

an image detector further comprising a liquid crystal television detector which detects light from said light source after it has been reflected from a biological target tissue and said light source and said detector are phase modulated in synchronicity; and a monitor which displays an image of an internal anatomical structure received from said image detector.

25. An imaging apparatus comprising a light source;

an image detector further comprising a photorefractive crystal which detects light from said light source after it has been reflected from a biological target tissue; and a monitor which displays an image of an internal anatomical structure received from said image detector.

26. A method for imaging an anatomical structure comprising illuminating a biological tissue;

wherein said step of illuminating comprises illuminating with a wavelength of between 700–900 nm;

detecting the reflected image from said biological target tissue; and displaying said reflected image on a monitor.

27. A method for imaging an anatomical structure comprising illuminating a biological target tissue;

bandpass filtering the light of interest;

detecting the reflected image from said biological target tissue; and displaying said reflected image on a monitor.

28. An imaging apparatus comprising a light source wherein said light source comprises a monochromatic source within the infrared range and wherein said monochromatic light source within the infrared range comprises means for illumination within the range of 700–900 nm;

an image detector which detects light from said light source after it has been reflected from a biological target tissue wherein said light source and said image detector are part of a unit; and a monitor which displays an image of an internal anatomical structure from said image detector.

29. The apparatus of claim 28 wherein said imaging apparatus further comprises a filter for eliminating light outside the wavelength of interest.

30. The apparatus of claim 29 wherein said filter comprises a bandpass filter.

31. The apparatus of claim 28 wherein said imaging apparatus further comprises a contrast enhancing element and wherein said monitor is part of the same unit as said image detector and said light source.

32. The apparatus of claim 28 wherein a helmet is part of the same unit as the image detector and said light source.

33. The apparatus of claim 32 wherein said imaging apparatus further comprises a filter for eliminating light outside the wavelength of interest.

34. The apparatus of claim 33 wherein said filter comprises a bandpass filter.

35. The apparatus of claim 34 further comprising a contrast enhancing element which includes a polarizing optical element in the path of incident light between said light source and said biological tissue and a polarizing selecting optical element in the path of the reflected light between the said biological tissue and said image detector.

36. An imaging apparatus comprising a light source wherein said light source comprises a monochromatic source within the infrared range and wherein said monochromatic light source within the infrared range comprises means for illumination within the range of 700–900 nm;
- an image detector which detects light from said light source after it has been reflected from a biological target tissue;
- a monitor which displays an image of an internal anatomical structure from said image detector; and
- a helmet comprising said light source and image detector.

37. The apparatus of claim 36 wherein said helmet further comprises said monitor.

38. The apparatus of claim 37 wherein said imaging apparatus further comprises a filter for eliminating light outside the wavelength of interest.

39. The apparatus of claim 37 wherein said helmet is made of three head straps.

40. The apparatus of claim 38 wherein said filter comprises a bandpass filter.

41. The apparatus of claim 40 further comprising a contrast enhancing element which includes a polarizing optical element in the path of incident light between said light source and said biological tissue and a polarizing selecting optical element in the path of the reflected light between the said biological tissue and said image detector.

42. An imaging apparatus comprising a light source wherein said light source comprises a monochromatic source within the infrared range and wherein said monochromatic light source within the infrared range comprises means for illumination within the range of 700–900 nm;
- an image detector which detects light from said light source after it has been reflected from a biological target tissue; and
- a monitor which displays an image of an internal anatomical structure from said image detector wherein said image detector and said monitor are part of a unit.

43. The apparatus of claim 42 wherein said imaging apparatus further comprises a filter for eliminating light outside the wavelength of interest.

44. An imaging apparatus comprising a light source wherein said light source comprises a monochromatic source within the infrared range and wherein said monochromatic light source within the infrared range comprises means for illumination within the range of 700–900 nm;
- an image detector which detects light from said light source after it has been reflected from a biological target tissue;
- a monitor which displays an image of an internal anatomical structure from said image detector; and
- a head piece attached to said monitor.

45. The apparatus of claim 44 wherein said imaging apparatus further comprises a filter for eliminating light outside the wavelength of interest.

46. An imaging apparatus comprising a light source wherein said light source comprises a source within the infrared range;
- an image detector which detects light form said light source after it has been reflected from a biological target tissue; and
- a monitor which displays an image of an internal anatomical structure received from said image detector wherein said monitor and said image detector are part of a unit.

47. The apparatus of claim 46 wherein the apparatus further comprises a contrast enhancing element.

48. The apparatus of claim 47 wherein said contrast enhancing element comprises a filter for eliminating light outside the wavelength of interest.

49. The apparatus of claim 47 wherein said image detector comprises a charge coupled device infrared camera.

50. The apparatus of claim 47 wherein said contrast enhancing element includes a polarizing optical element in the path of incident light between said light source and said biological tissue and a polarizing selecting optical element in the path of the reflected light between the said biological tissue and said image detector.

51. An imaging apparatus comprising a light source wherein said light source comprises a source within the infrared range;
- an image detector which detects light from said light source after it has been reflected from a biological target tissue wherein said image detector and said light source are part of a unit; and
- a monitor which displays an image of an internal anatomical structure received from said image detector.

52. The apparatus of claim 51 wherein the apparatus further comprises a contrast enhancing element.

53. The apparatus of claim 52 wherein said contrast enhancing element comprises a filter for eliminating light outside the wavelength of interest.

54. The apparatus of claim 52 wherein said image detector comprises a charge coupled device infrared camera.

55. The apparatus of claim 52 wherein said contrast enhancing element includes a polarizing optical element in the path of incident light between said light source and said biological tissue and a polarizing selecting optical element in the path of the reflected light between the said biological tissue and said image detector.

56. An imaging apparatus comprising a light source wherein said light source comprises a source within the infrared range;
- an image detector which detects light from said light source after it has been reflected from a biological target tissue;
- a helmet comprising said light source and said image detector;
- and a monitor which displays an image of an internal anatomical structure received from said image detector.

57. The apparatus of claim 56 wherein the apparatus further comprises a contrast enhancing element.

58. The apparatus of claim 57 wherein said contrast enhancing element comprises a filter for eliminating light outside the wavelength of interest.

59. The apparatus of claim 57 wherein said image detector comprises a charge coupled device infrared camera.

60. The apparatus of claim 57 wherein said contrast enhancing element includes a polarizing optical element in the path of incident light between said light source and said biological tissue and a polarizing selecting optical element in the path of the reflected light between the said biological tissue and said image detector.

61. An imaging apparatus comprising a light source wherein said light source comprises a source within the infrared range;

an image detector which detects light from said light source after it has been reflected from a biological target tissue; and a helmet comprising said image detector, said light source and a monitor which displays an image of an internal anatomical structure received from said image detector.

62. The apparatus of claim 61 wherein the apparatus further comprises a contrast enhancing element.

63. The apparatus of claim 62 wherein said contrast enhancing element comprises a filter for eliminating light outside the wavelength of interest.

64. The apparatus of claim 62 wherein said image detector comprises a charge coupled device infrared camera.

65. The apparatus of claim 62 wherein said contrast enhancing element includes a polarizing optical element in the path of incident light between said light source and said biological tissue and a polarizing selecting optical element in the path of the reflected light between the said biological tissue and said image detector.

66. An imaging apparatus comprising a light source;

an image detector further comprising a video camera which detects light from said light source after it has been reflected from a biological target tissue wherein said image detector and said light source are part of a unit; and a monitor which displays an image of an internal anatomical structure received from said image detector.

67. The apparatus of claim 66 wherein said imaging apparatus further comprises a filter for eliminating light outside the wavelength of interest.

68. The apparatus of claim 67 wherein said filter comprises a bandpass filter.

69. The apparatus of claim 66 wherein said imaging apparatus further comprises a contrast enhancing element and wherein said monitor is part of the same unit as said image detector and said light source.

70. The apparatus of claim 66 further comprising a contrast enhancing element which includes a polarizing optical element in the path of incident light between said light source and said biological tissue and a polarizing selecting optical element in the path of the reflected light between the said biological tissue and said image detector.

71. The apparatus of claim 66 wherein a helmet is part of the same unit as the image detector and said light source.

72. The apparatus of claim 71 wherein said imaging apparatus further comprises a filter for eliminating light outside the wavelength of interest.

73. The apparatus of claim 72 wherein said filter comprises a bandpass filter.

74. An imaging apparatus comprising a light source;

an image detector further comprising a video camera which detects light from said light source after it has been reflected from a biological target tissue;

a monitor which displays an image of an internal anatomical structure from said image detector; and a helmet comprising said light source and image detector.

75. The apparatus of claim 74 wherein said helmet further comprises said monitor.

76. The apparatus of claim 74 further comprising a contrast enhancing element which includes a polarizing optical element in the path of incident light between said light source and said biological tissue and a polarizing selecting optical element in the path of the reflected light between the said biological tissue and said image detector.

77. The apparatus of claim 75 wherein said imaging apparatus further comprises a filter for eliminating light outside the wavelength of interest.

78. The apparatus of claim 75 wherein said helmet is made of three head straps.

79. The apparatus of claim 77 wherein said filter comprises a bandpass filter.

80. An imaging apparatus comprising a light source;

an image detector further comprising a video camera which detects light from said light source after it has been reflected from a biological target tissue; and a monitor which displays an image of an internal anatomical structure from said image detector wherein said image detector and said monitor are part of a unit.

81. The apparatus of claim 80 wherein said imaging apparatus further comprises a filter for eliminating light outside the wavelength of interest.

82. An imaging apparatus comprising a light source;

an image detector further comprising a video camera which detects light from said light source after it has been reflected from a biological target tissue;

a monitor which displays an image of an internal anatomical structure from said image detector; and a head piece attached to said monitor.

83. The apparatus of claim 82 wherein said imaging apparatus further comprises a filter for eliminating light outside the wavelength of interest.

84. An imaging apparatus comprising:

a light source;

an image detector which detects light from said light source transmitted through biological target tissue;

a monitor which receives and displays image information from said image detector;

a head piece attached to said monitor; and a contrast enhancing element which includes a first polarizing optical element in the path of incident light between said light source and said biological tissue and a second polarizing optical element in the path of the transmitted light between the non-light source side of the tissue and said image detector.

85. An imaging apparatus comprising a light source in the infrared image:

an image detector which detects light from said light source transmitted through biological target tissue;

a monitor which receives and displays image information from said image detector;

a head piece attached to said monitor; and a contrast enhancing element which includes a first polarizing optical element in the path of incident light between said light source and said biological tissue and a second polarizing optical element in the path of the transmitted light between the non-light source side of the tissue and said image detector.

86. An imaging apparatus comprising:

a light source;

an image detector which detects light from said light source reflected from a biological target tissue;

a monitor which receives and displays image information from said image detector;

a head piece attached to said monitor; and a contrast enhancing element which includes a polarizing optical element in the path of incident light between said light source and said biological tissue and a polarizing selecting optical element in the path of the reflected light between the said biological tissue and said image detector.

87. An imaging apparatus comprising a light source in the infrared image:

an image detector which detects light from said light source reflected from a biological target tissue;

a monitor which receives and displays image information from said image detector; and a contrast enhancing element which includes a polarizing optical element in the path of incident light between said light source and said biological tissue and a polarizing selecting optical element in the path of the reflected light between the said biological tissue and said image detector.

88. A method of using the apparatus of claims 1, 28, 36, 42 or 44 wherein said monitor is worn by the apparatus operator.

89. A method of using the apparatus of claim 1 or 28 wherein said unit is worn by the apparatus operator.

90. A method of using the apparatus of claim 1 or 28 wherein both said unit and said monitor are worn by the apparatus operator.

* * * * *